(12) United States Patent
Samson et al.

(10) Patent No.: US 7,413,557 B2
(45) Date of Patent: Aug. 19, 2008

(54) BREAST PUMP

(75) Inventors: Ilan Samson, London (GB); Ian Webb, London (GB)

(73) Assignees: Ilan Sampson, London (GB); Jackel International Limited, Northumberland (GB)

( * ) Notice: Subject to any disclaimer, the term of this patent is extended or adjusted under 35 U.S.C. 154(b) by 0 days.

(21) Appl. No.: 10/518,900

(22) PCT Filed: Jun. 19, 2003

(86) PCT No.: PCT/GB03/02633

§ 371 (c)(1),
(2), (4) Date: Sep. 27, 2005

(87) PCT Pub. No.: WO04/000390

PCT Pub. Date: Dec. 31, 2003

(65) Prior Publication Data

US 2006/0111664 A1    May 25, 2006

(30) Foreign Application Priority Data

Jun. 24, 2002    (GB)    ................................. 0214525.8

(51) Int. Cl.
*A61M 1/06*    (2006.01)
(52) U.S. Cl. ........................................................ 604/74
(58) Field of Classification Search .............. 604/73–76
See application file for complete search history.

(56) References Cited

U.S. PATENT DOCUMENTS 3,399,695 A * 9/1968 Stehlin ........................ 137/551
3,769,982 A * 11/1973 Schulte ......................... 604/10
4,680,028 A    7/1987 Stuart
4,794,915 A    1/1989 Larsson (Continued)

FOREIGN PATENT DOCUMENTS

EP    0 198 469    10/1986

(Continued)

*Primary Examiner*—Kevin C. Sirmons
*Assistant Examiner*—Elizabeth R Macneil
(74) *Attorney, Agent, or Firm*—Stites & Harbison PLLC; Ross F. Hunt, Jr.

(57) ABSTRACT

A breast pump comprises a body member (2) including a breast engaging portion (4) shaped to engage a region of a user's breast, a container (32) attached to the body member (2), valve means (28) between the body member (2) and the container (32), and, within the body member (2), a sleeve (12) sealing the interior of the body member (2) from the atmosphere, the sleeve (12) being selectively movable from a rest condition to a displaced condition by actuating means (14) operatively connected to the sleeve (12), movement of the sleeve (12) from the rest condition to the displaced condition creating an increasing volume of reduced pressure within the body member (2) whereby firstly the valve means (28) is closed to prevent evacuation of the container (32), and whereby milk is expressed by the user into the body member (2), and return movement of the sleeve (12) from the displaced condition to the extended condition releasing the reduced pressure allowing the valve to open, the expressed milk flowing through the valve means (28) and into the container (32), the configuration of the sleeve (12) or the material of the sleeve (12) being such as to substantially prevent stretching of the sleeve (12) on movement between the rest and displaced conditions.

24 Claims, 8 Drawing Sheets

U.S. PATENT DOCUMENTS

| | | | |
|---|---|---|---|
| 4,813,932 A * | 3/1989 | Hobbs | 604/74 |
| 5,009,638 A | 4/1991 | Riedweg et al. | |
| 5,049,126 A | 9/1991 | Larsson | |
| 5,415,632 A | 5/1995 | Samson | |
| 5,749,850 A * | 5/1998 | Williams et al. | 604/74 |
| 5,843,029 A * | 12/1998 | Bachman et al. | 604/74 |
| 5,971,952 A | 10/1999 | Medo | |
| 6,110,140 A * | 8/2000 | Silver | 604/74 |
| 6,383,164 B1 | 5/2002 | McCormick et al. | |
| 6,387,072 B1 | 5/2002 | Larsson | |
| 6,461,324 B1 | 10/2002 | Schlensog | |
| 6,579,258 B1 | 6/2003 | Atkin et al. | |
| 6,749,582 B2 * | 6/2004 | Britto et al. | 604/74 |
| 2001/0016708 A1 * | 8/2001 | Kong et al. | 604/152 |
| 2003/0153869 A1 * | 8/2003 | Ytteborg | 604/74 |

FOREIGN PATENT DOCUMENTS

| | | |
|---|---|---|
| EP | 0 466 462 | 1/1992 |

\* cited by examiner

BREAST PUMP

This invention relates to a breast pump for use by a mother of a young infant.

It is well established that a mother's natural milk is preferable to, for example, cow's milk or various feeding formulae for feeding infants, and various types of pumping devices have been devised to express a mother's milk from her breasts for more convenient subsequent feeding to the infant.

Although manually operated pumps have been found to be less costly and more practical than electrically operated pumps, most existing manual pumps still suffer from various disadvantages.

In particular, it is well-established practice to incorporate a piston-cylinder assembly within the pump, movement of the piston in the cylinder creating the vacuum necessary to extract the milk from the breast of the user, subsequent release of the vacuum allowing the extracted milk to pass through a valve assembly and into an associated container.

However, with such an arrangement, and to ensure creation of the vacuum, it is necessary for the piston cylinder assembly, and in particular the seal between the piston and the cylinder, to be accurately manufactured to ensure a fluid-tight seal. Such critical and precise engineering, and the requirement for an accurately machined seal, can prove expensive.

Furthermore movement of the piston within the cylinder, and in particular the continuous sealing engagement of the piston with the cylinder, being pressed together by suction forces, creates friction within the pump that needs to be overcome by the user and whereby energy is wasted.

It has been proposed to replace the piston cylinder arrangement of a breast pump with a cup-shaped diaphragm of silicone or flexible elastomeric material the peripheral regions of which are fixed and the base portion of which is moved or rolled generally axially of the diaphragm through the peripheral regions to create the vacuum necessary to express milk.

However, as the region of reduced pressure within the pump is created, the material of the diaphragm is stretched due to the pressure differential thereacross, this stretching increasing on decrease of pressure within the pump.

Thus, in order to continue movement of the diaphragm it is necessary to overcome this stretching of the material of the diaphragm, whereby considerable extra energy has to be expended by the user.

It would be desirable to be able to provide a breast pump capable of more economical and less precise manufacture than heretofore, and which was more energy efficient than heretofore.

According to the present invention there is provided a breast pump comprising a body member including a breast engaging portion shaped to engage a region of a user's breast, a container attached to the body member, and valve means between the body member and the container, characterised by, within the body member, a sleeve sealing the interior of the body member from the atmosphere, the sleeve being selectively movable from a rest condition to a displaced condition by actuating means operatively connected to the sleeve, movement of the sleeve from the rest condition to the displaced condition creating an increasing volume of reduced pressure within the body member whereby firstly the valve means is closed to prevent evacuation of the container, and whereby milk is expressed by the user into the body member, and return movement of the sleeve from the displaced condition to the extended condition releasing the reduced pressure allowing the valve to open, the expressed milk flowing through the valve means and into the container, the configuration of the sleeve or the material of the sleeve being such as to substantially prevent stretching of the sleeve on movement between the rest and displaced conditions.

It will be appreciated that the return movement of the sleeve to the extended condition brings the reduced pressure back up towards atmospheric, this in turn, together with the pressure of any milk resting above the valve, opening the valve, starting to feed the milk into the container, completing release of the milk through the valve once the return movement of the sleeve member has restored the pressure to atmospheric (or slightly above this) to counteract the milk's surface tension. Furthermore the sleeve is made such as to substantially prevent stretching without impairing flexibility.

Thus it will be appreciated that, with such an arrangement, where, on displacement of the sleeve, the volume within the body member available to receive milk expressed by the user is increased, with a consequential reduction in the pressure therein and the creation of the vacuum necessary to express the milk, the non-stretch nature of the sleeve reduces the effort required to effect the displacement compared with conventional arrangements.

In some embodiments of the invention, the sleeve is of generally concertina shape, and is selectively movable between an extended rest condition and a compacted displaced condition.

Preferably the concertina shape has a closed base thereto at least part of which is substantially rigid, movement of the sleeve being by pulling the base from inside the sleeve so as to contract its length.

The configuration of such a sleeve is such as to ensure substantially no stretching thereof when under suction in the only possible direction, namely radially, on movement between the extended condition and the displaced condition. Furthermore, as the projected surface area of the bellows that is exposed to the aforementioned stretching differential pressure reduces as the sleeve is compacted, the stretching force does not continue to grow with the increase in the generated suction.

Preferably the concertina sleeve is of a flexible material, for example silicone or a thermoplastic elastomer such as polyurethane, the inherent properties of which are such that, on release of the lever arm by the user, the sleeve returns to its extended condition within the body member.

In other embodiments of the invention the sleeve acts essentially as a 'roll diaphragm' and comprises a substantially non-stretch material, and includes, for example a flexible layer, such as silicone or a thermoplastic elastomer, to which is bonded or which is inlaid with a substantially non-stretch layer such as a fabric mesh. Thus the material of the sleeve itself is such as to resist stretching on movement between the rest and displaced conditions without impairing its flexibility.

The actuating means may comprise a lever arm pivotally mounted at an intermediate region thereof to the body member, one end extent of the lever arm being for engagement by the user, and the other end extent being operatively connected to the sleeve.

One end of the sleeve may be secured between a collar and a defining wall of the body member whereby the interior of the sleeve is sealed from the interior of the body member, the other end of the sleeve being closed.

Conveniently the other, closed end of the sleeve carries an end plate, a link pin extending axially within the sleeve and through the collar to interconnect the end plate and the other end extent of the lever arm whereby, on pivoting movement of the lever arm by the user, the link pin is moved substantially axially of the sleeve to compact the sleeve.

The end plate, link pin, sleeve and lever arm may comprise an integral unit, and may incorporate flexible joints at one or both ends of the link pin.

The actuating means may comprise an operating member one end of which is secured to a closed end of the sleeve and the other end of which carries a thumb-receiving element for receiving the thumb of a user.

Preferably a handle member is provided as a rest and grip for the fingers of the actuating hand, said handle being rigidly secured to the pump body, the arrangement being such that, on location of the thumb in the thumb-receiving element, and on pulling of the thumb towards the fingers, the base of the sleeve is pulled in the direction generally away from the breast.

In a preferred embodiment of the invention the valve means between the body member and the container comprise a duck bill type one way valve.

By way of example only, embodiments of the invention will now be described in greater detail with reference to the accompanying drawings of which:

FIG. 1 is a vertical section through a first breast pump according to the invention with the sleeve in its rest condition, FIGS. 2 and 3 are vertical sections through part of the pump of FIG. 1 with the sleeve in a partly displaced condition and a fully displaced condition respectively, and FIG. 4 is a vertical section through a second breast pump according to the invention.

Referring to FIGS. 1 to 3, the illustrated breast pump comprises a body member indicated generally at 2 preferably moulded from a thermoplastic elastomer such as polypropylene or polycarbonate, and including a generally conical breast engaging portion or horn 4 shaped to receive part of the breast of a user with the nipple located substantially centrally of the horn 4.

The horn 4 feeds into a tubular portion 6 of the body member 2, the tubular portion 6 itself feeding into a main volume 8 of the body member 2.

The body member 2 includes an upwardly open top end onto which may be attached an optional retaining annular collar 10. Secured between the collar 10 and the top end of the body member 2 is the annular flange of one end of a hollow, concertina-shaped sleeve 12 of an elastic material such a polyurethane which extends into the body member 2, the other end of the sleeve 12 within the body member 2 being closed. The arrangement is such that the co-operation between the collar 10 and the one end of the sleeve 12 seals the top end of the body member, the sleeve 12 thereby constituting a dividing barrier between the sealed interior of the body member and the external atmosphere, with the hollow interior of the sleeve 12 communicating with the atmosphere outside the body member 2.

Alternatively the sealing connection between the open end of the body member 2 and the flange on the sleeve 12 may be effected by the elasticity of the flange wrapping over the rim of the body member without a collar 10.

An operating lever arm is indicated generally at 14 and is pivotally mounted to the body member at 16, the lever arm 14 including a first end extent 18 for engagement by the user to actuate the pump as will be detailed below, and a second end extent 20 for operative connection to the sleeve 12.

More particularly, the other end of the sleeve 12 has mounted externally or internally thereon a rigid end plate 22 to the centre of which one end of a link pin 24 is pivotally mounted. The pin 24 extends axially of the sleeve 12 and through the collar 10 with the other end of the pin 24 being attached to the second end extent 20 of the lever arm 14.

It will thus be appreciated that, on pivoting of the lever arm 14 to move the first end extent 18 thereof towards the body member 2, the link pin 24 is raised by the resulting movement of the second end extent 20 of the lever arm 14 away from the body member 2, thus drawing the end plate 22 upwardly therewith and compacting the sleeve 12 as shown in FIGS. 2 and 3. The arcuate movement of the second end extent 20 of the lever arm 14 is readily accommodated by a combination of the pivotal attachment of the link pin 24 to the end plate 22, the nature of the attachment of the other end of the pin 24 to the second end extent 20 of the lever arm 14, and the generally flexible nature of the material of the sleeve 12.

The sleeve 12 is of an flexible material, for example silicone or a thermoplastic elastomer such as polyurethane, and has an inherent memory whereby the sleeve 12 tends to return towards the extended condition shown in FIG. 1. Thus, on release of any pivoting force from the first end extent 18 of the lever arm 14, the sleeve 12 extends to the rest condition of FIG. 1, the balance of the lever arm 14 being such as to encourage the sleeve 12 and the arm 14 to return to their rest conditions as shown in FIG. 1.

The lower end of the body member 2 comprises an outlet 26 to which is mounted a duck bill type one way valve 28.

The pump may optionally include an adaptor 30 by which the body member 2 is attached to a container 32, conveniently by a screw thread.

The described breast pump operates as follows. The user takes hold of the container 2 and applies the horn 4 of the pump to her breast with sufficient pressure to seal against the breast. She then pivots the lever arm 14 about the pivot point 16 whereby, as detailed above, the concertina sleeve 12 is compacted. Thus the volume 8 between the outside of the sleeve 12 and the inside of the surrounding body member 2 is increased. As this volume is sealed from the atmosphere by way of the user's breast, the one-way valve 28 and the co-operation between the collar 10 and the one end of the sleeve 12, the pressure in the volume 8 is reduced to create a vacuum whereby milk is expressed from the breast and into the volume 8. In view of the concertina or convoluted shape of the sleeve, there is little tendency for the material of the sleeve 12 to stretch radially outward despite the pressure differential thereacross—there is a corresponding decrease in the projected surface area of the sleeve as the pressure differential increases which maintains substantially constant the force necessary to effect continuous compaction of the sleeve.

On release of the lever arm 14, the sleeve 12 returns to its extended condition in view of its inherent elasticity and the supplementary effect of the lever arm 14 to increase the pressure within the volume 8, that is releasing the suction therein allowing the valve to open and milk to flow and pump the milk through the valve 28 into the container 32 as a result of the vacuum release, this flow of milk from the body member 2 to the container 32 being supplemented by gravity.

This procedure can be repeated until sufficient milk has been expressed or until all available milk has been expressed.

The provision of the concertina sleeve 12 as the pumping element substantially eliminates the requirement for accurate machining, in that there is no need for the sleeve 12 to be guided during its compaction and extension movements. Furthermore, and as detailed above, there is substantial relative movement available between the lever arm 14 and the sleeve 12, in particular in view of the relatively flexible mounting of the link pin 24 to the second end extent 20 of the lever arm 14. Additional flexibility may be achieved by providing a link pin 24 of a non-rigid, bendable material. Conveniently the end plate 22, the link pin 24, the sleeve 12 and the lever arm 14 are manufactured as an integral unit.

Clearly the precise construction and orientations of the component parts of the pumping mechanism may vary from those described and illustrated without departing from the scope of the invention. For example the central axis of the sleeve 12 may be other than substantially vertical, for example substantially horizontal, the actuating means may be other than a lever arm 14 and may be movable other than towards the container 32, for example away from the container and by the thumb of the user, and the valve means may be other than a duck bill one way valve. The sleeve may be of a suitable elastic material such as a thermoplastic elastomer, for example polyurethane, or of silicone or of natural rubber, while the body member 2 and horn 4 may be of a suitable thermoplastic material such as polypropylene or polycarbonate. The container 32 is conveniently of a translucent or transparent plastic material. Actuating means may be electric or mechanical, hand-held or attached such as battery powered or a separate remote mains powered unit.

Referring to FIG. 4 there is shown an alternative embodiment of the invention the operation of which is substantially the same as that of the embodiment of FIGS. 1 to 3 and which will therefore not be described in detail again.

Instead of the concertina sleeve 12 there is provided a sleeve 12' a free end of which is mounted to the body 2' and the other closed end of which extends transversely of the body 2' to seal the interior of the body 2' from the atmosphere.

The sleeve 12' is of a substantially non-stretch material, comprising a non-stretching flexible material or a layer of elastic material, for example silicone or a thermoplastic elastomer such as polyurethane, to which is bonded, inlaid or insert moulded a substantially non-stretch layer such as a fabric mesh.

One end of a lever 14' is secured centrally to the closed end of the sleeve 12' externally of the body 2', the other end of the lever 14' comprising an element 40 adapted to receive the thumb of a user, which element 40 may be ring-shaped as shown or of other suitable configuration.

Displacement of the sleeve 12' from the rest condition shown in FIG. 4 to a displaced condition to create the required volume of reduced pressure within the body 2' is achieved by engaging the thumb of the user in the portion 40 and moving the thumb away from the pump in the direction of arrow T. This arrangement obviates the cost and energy loss associated with a hinged lever mechanism.

The non-stretch nature of the material of the sleeve 12' ensures an energy-efficient arrangement.

Although the embodiment of FIGS. 1 to 3, which includes a concertina-shaped sleeve, shows a lever arm as the actuating means, it will be appreciated that other actuating means, such as a thumb-receiving element similar to that shown in FIG. 4, could be used.

Similarly, although the embodiment of FIG. 4, which includes a 'roll diaphragm' type sleeve, shows a thumb-receiving element as the actuating means, it will be appreciated that other actuating means, such as a lever arm similar to that shown in FIGS. 1 to 3, could be used.

Thus there are provided breast pumps, which may be operated manually or electrically, which are substantially more energy efficient than heretofore, this efficiency being achieved either by the configuration or the material of the sleeve, or by both—i.e. the material of the sleeve 12 may be non-stretch—and which can be manufactured more economically and with less precision than heretofore.

Reference will now be made to the generally conical breast engaging portion of the pump hereinafter referred to as the horn.

Conventionally, the horn of a breast pump is shaped to engage a region of the mother's breast whereby a sealed chamber is created in the pump and whereby a vacuum can be created in the chamber to express milk from the breast.

Heretofore horns have commonly been moulded from relatively rigid materials such as polycarbonate, which results in certain disadvantages not the least of which are potential discomfort to the user, the possibility of non-sealing engagement with the breast, and the inability of the user to manually stimulate her breast in accordance with the Marmet technique to supplement the suction effect of the pump.

In order to improve the comfort of the user, it has been proposed to provide relatively soft inserts typically hooking over the outer edge of the horn or being pressed into the interior of the horn.

However, it will be appreciated that such inserts, being separate from the horn, require assembly into and disassembly from the horn, have to be removed from the horn for cleaning purposes, and don't allow manual stimulation of her breast by the user.

It has also been proposed to configure certain of the inserts in an attempt to create an arrangement which, when subjected to the suction effect of the associated pump, serves to further stimulate the breast whereby expressing of milk is improved.

Such inserts include a series of resilient, circumferentially spaced petals surrounding the nipple and arranged to apply a peristaltic pressure thereto by being moved in and out in accordance with the negative pressure created by the pump.

However, such an arrangement suffers from the disadvantage that the movement of the petals is out of synchronism with the pressure within the pump, when milk is being expressed, the petals are drawn away from the breast, and, with positive pressure within the pump, when milk is not being expressed but is being fed to a container, the petals are moved towards, to engage and stimulate, the breast.

Furthermore, such an insert does not enable manual stimulation of the breast.

It would be desirable to be able to provide a breast pump having a horn which was comfortable to the user and which enabled manual stimulation of the breast by the user whilst still supporting the breast.

Accordingly there is provided a breast pump having a horn shaped to engage a region of a user's breast, the horn being of a relatively rigid material such as polypropylene or polycarbonate and having bonded thereto at least one region of relatively soft, elastic material such as a thermoplastic elastomer, the relatively soft material of the or each region infilling an associated aperture through the relatively rigid material to comprise the thickness of the horn at said region.

Thus it will be appreciated that the soft material is an integral part of the horn, being bonded to the rigid material, and provides one or more regions of elasticity to the horn whereby the user can manipulate said region(s) which in turn stimulates the underlying area(s) of the breast, conveniently the nipple or an adjacent area, the rigid material providing the necessary support to the breast.

There may be two opposed regions of relatively soft, elastic material remote from the open end of the horn, one for location above the breast and one for location below the breast adjacent the nipple for manipulation by the thumb and a finger of the user.

Conveniently the whole of the internal area of the rigid material is lined with said soft material, while the outer peripheral edge of the horn may comprise a lip of said soft material encasing the periphery of the rigid material.

Preferably the horn comprises a two-shot moulding with the relatively soft, elastic material permanently bonded to the relatively rigid material by virtue of the inherent characteristics of the materials.

By way of example only, a pump incorporating the preferred horn will now be described in greater detail with reference to the accompanying drawings of which:

Figure 1:
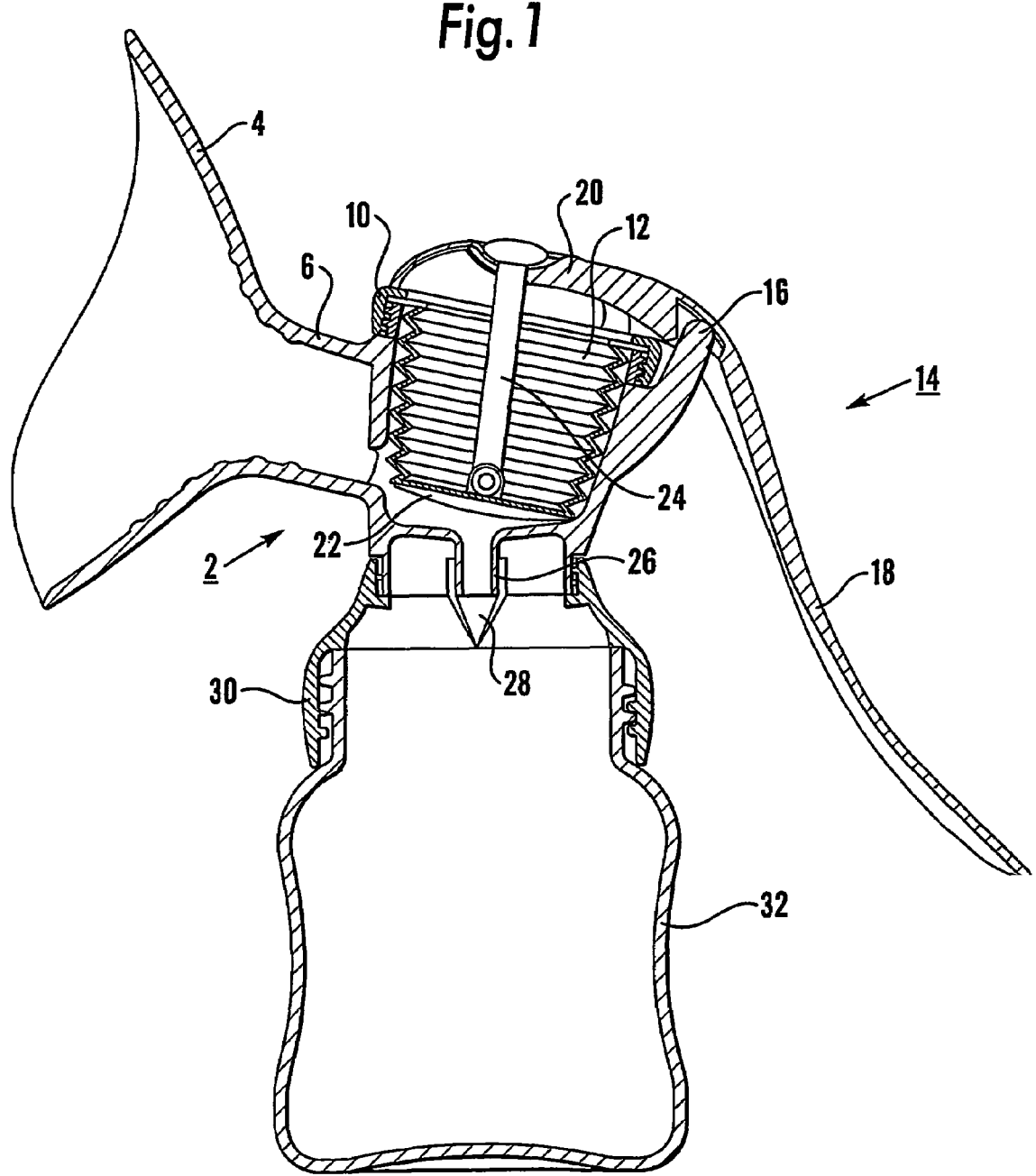
Figure 2:
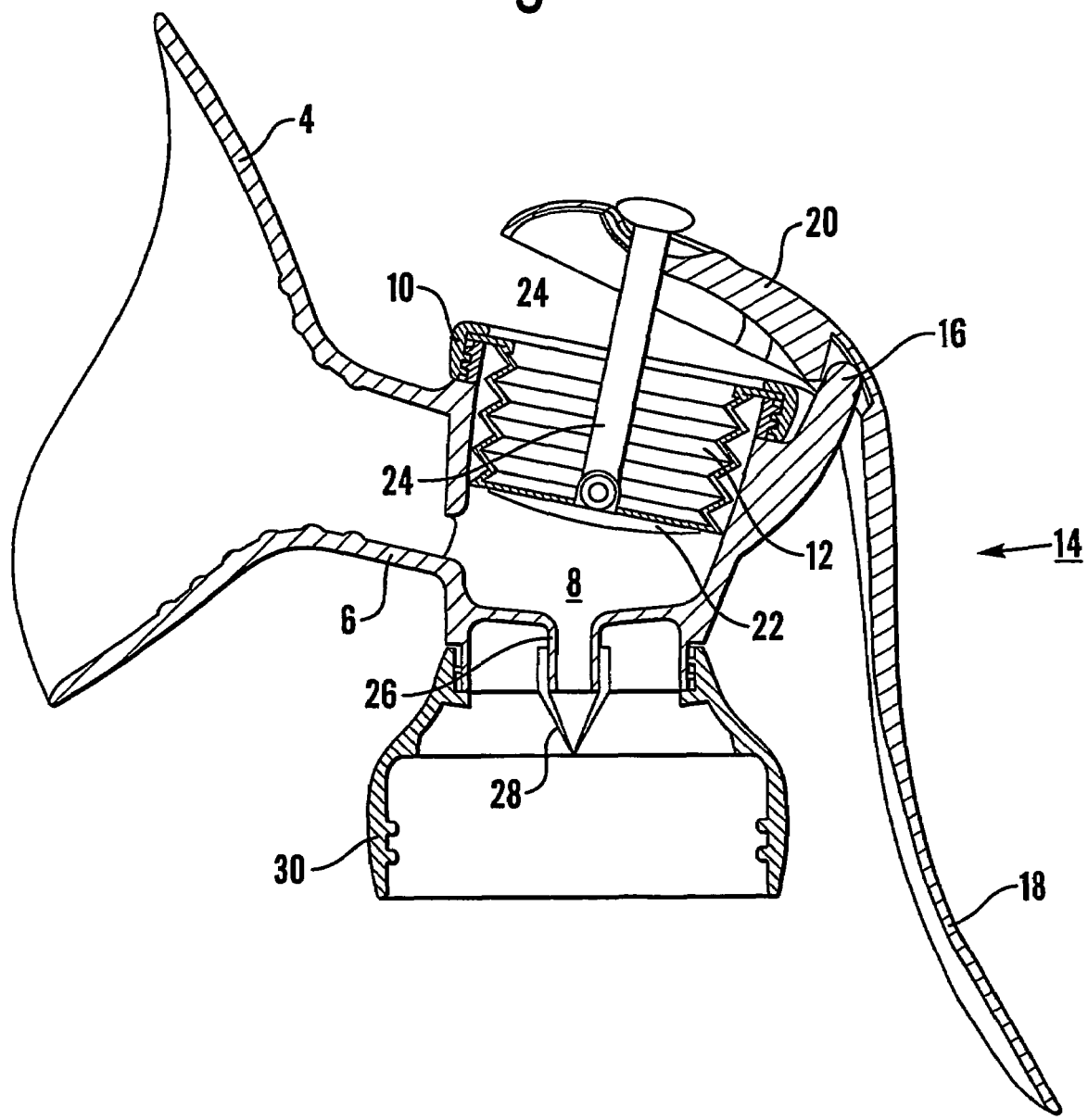
Figure 3:
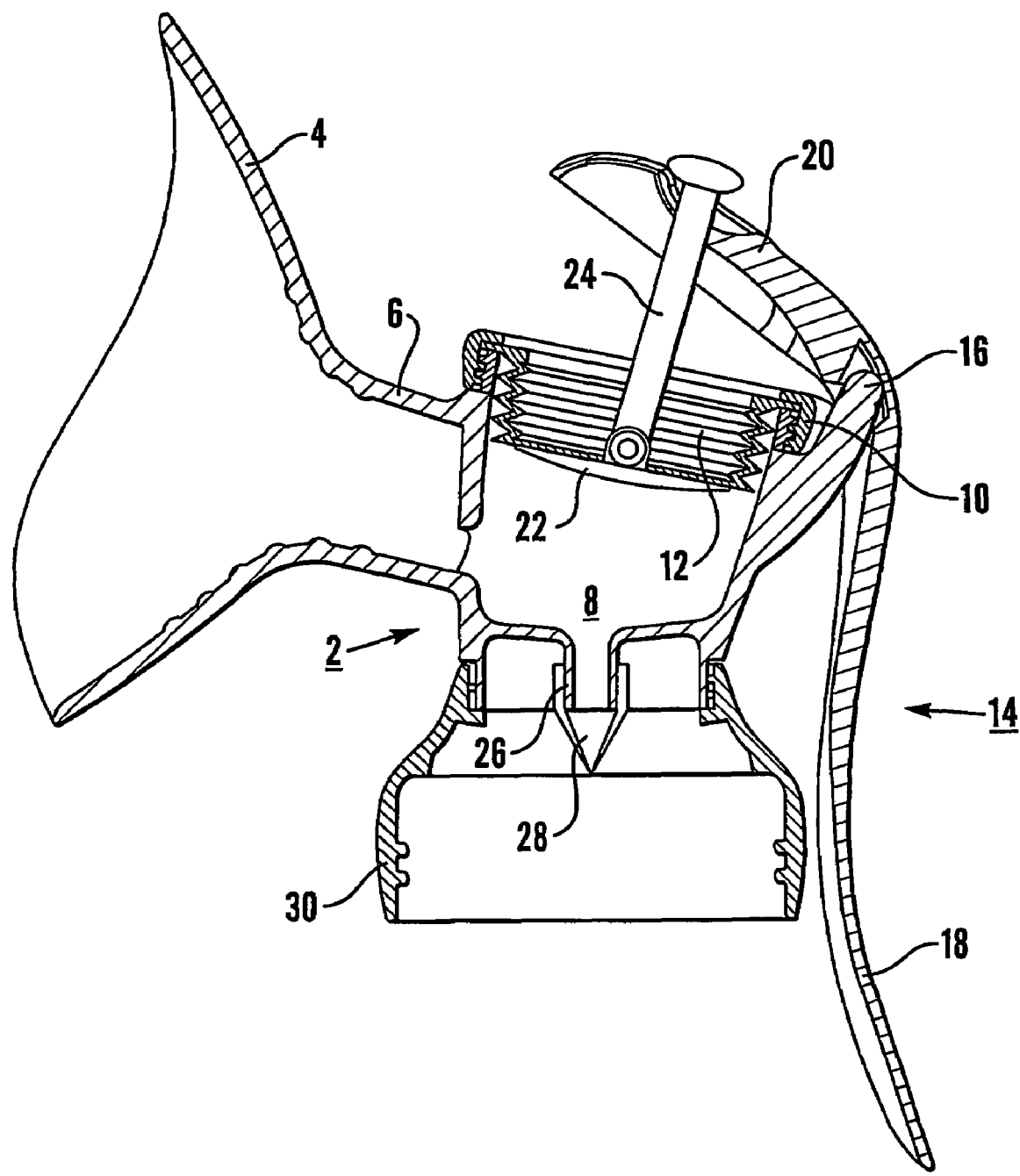
Figure 4:
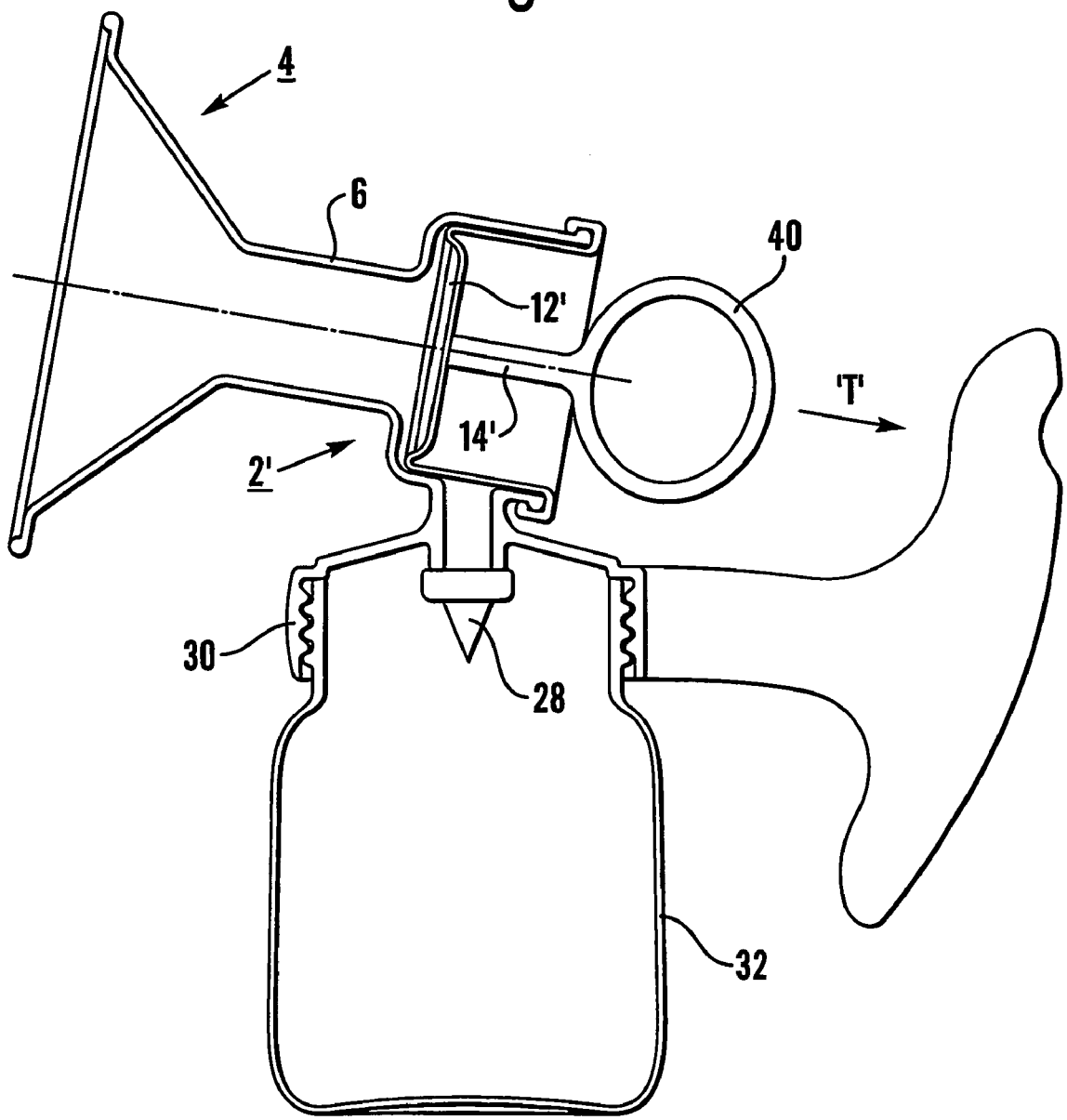
Figure 5:
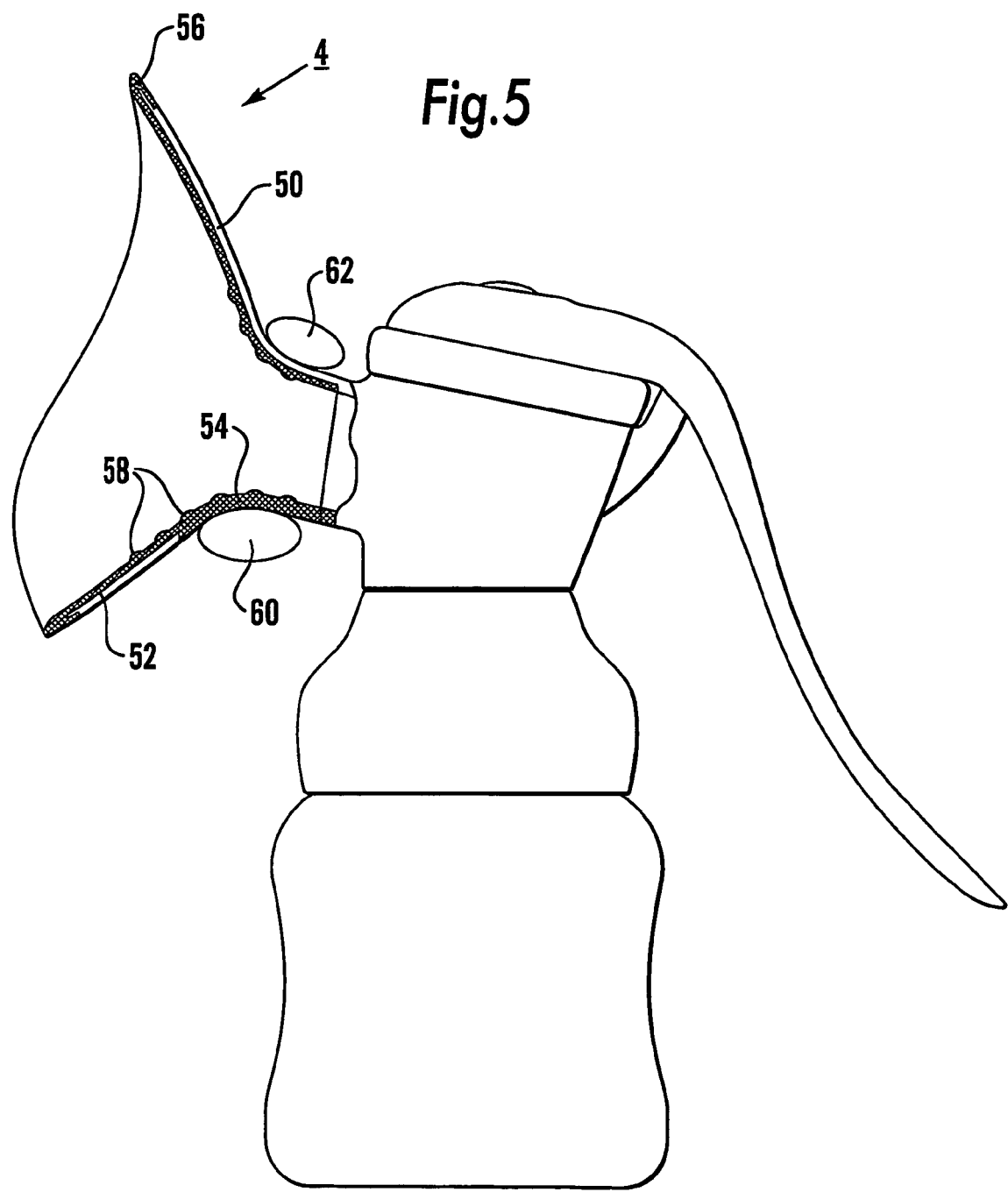
FIGS. 5 and 6 show pumps with two alternative horns.

Referring to FIG. 5 there is shown a horn indicated generally at 4 which comprises a rigid shell 50 typically of polypropylene or polycarbonate in the lower regions of which, adjacent the tubular portion 6, is formed an aperture.

The rigid shell 50 is lined with a layer 52 of a soft flexible elastic material such as a thermoplastic elastomer which is bonded to the shell 50 and which infills, at 54, the aperture in the shell 50 to comprise the full thickness of the horn at that region. The layer 52 includes a peripheral lip 56 which surrounds the outer peripheral edge of the shell 50.

Integrally formed on the inner surface of the soft layer 52 in the region of the infill 54 and in the region above this infill may be a plurality of dimples 58 or similar small embossed areas.

The described horn is manufactured by a two-shot moulding process, the first shot forming the rigid shell 50 and the second shot moulding on the soft layer 52 whereby the two layers are permanently bonded together.

Figure 7:
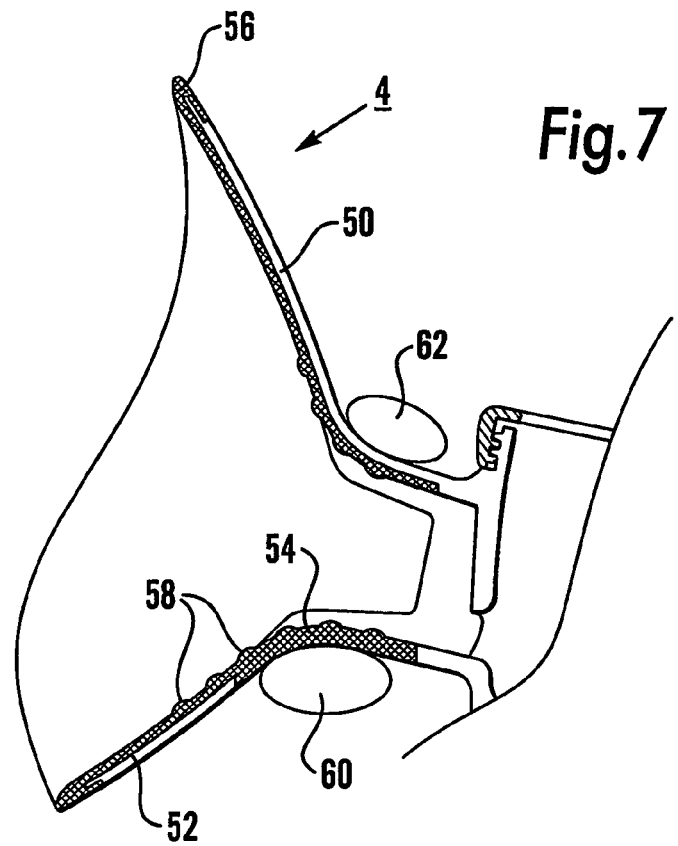
FIGS. 7 and 8 show the horn of FIGS. 5 and 6 positioned on a breast.

In use of the described horn, and referring in particular to FIG. 7, the soft layer 54 together with the lip 56, ensures a comfortable fit on the breast, while the presence of the soft infill at 54 enables the mother to manipulate her breast using her thumb 60 together with her finger 62. The strategically positioned dimples further assist in this stimulation.

Figure 6:
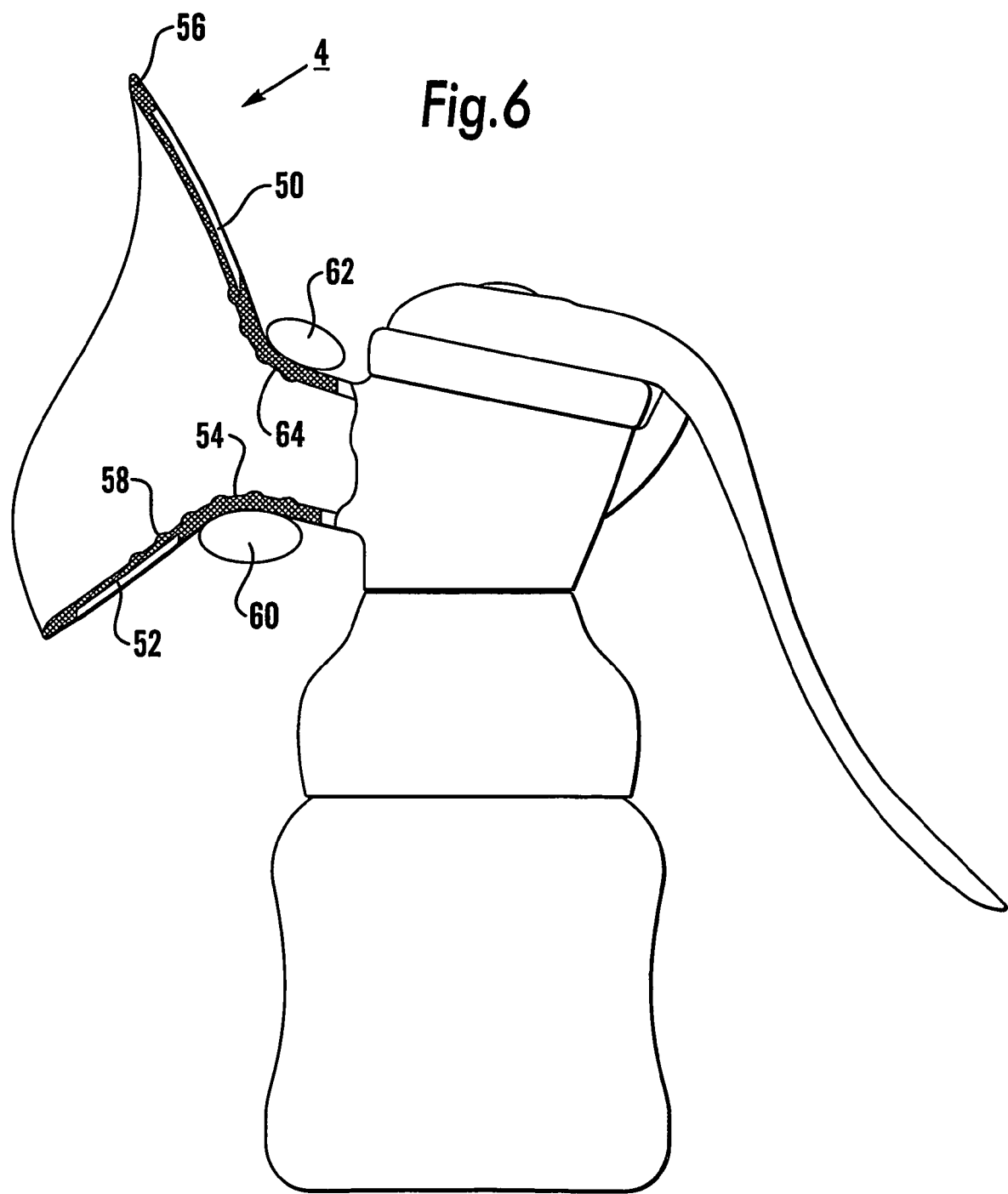
Figure 8:
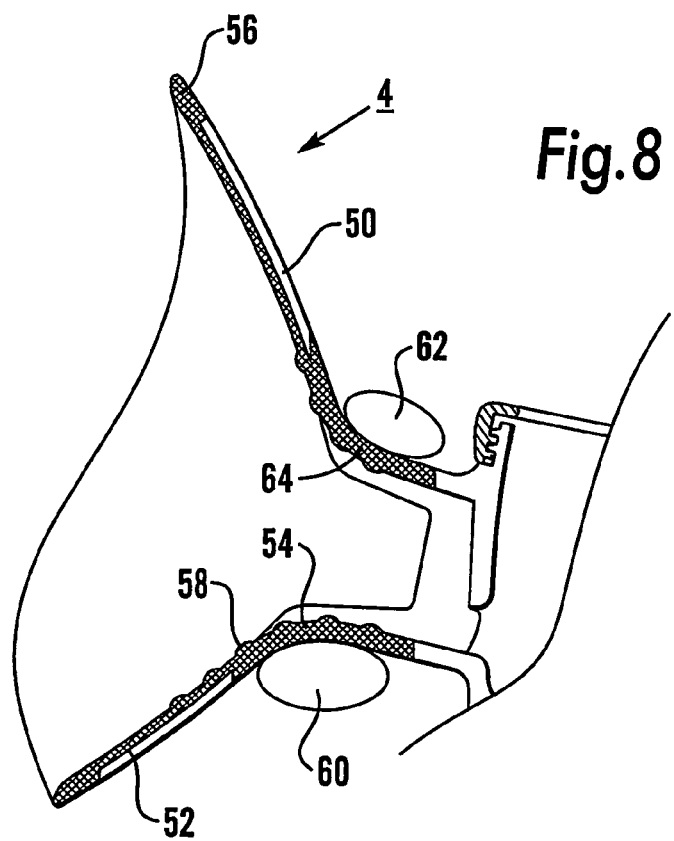
Figure 9:
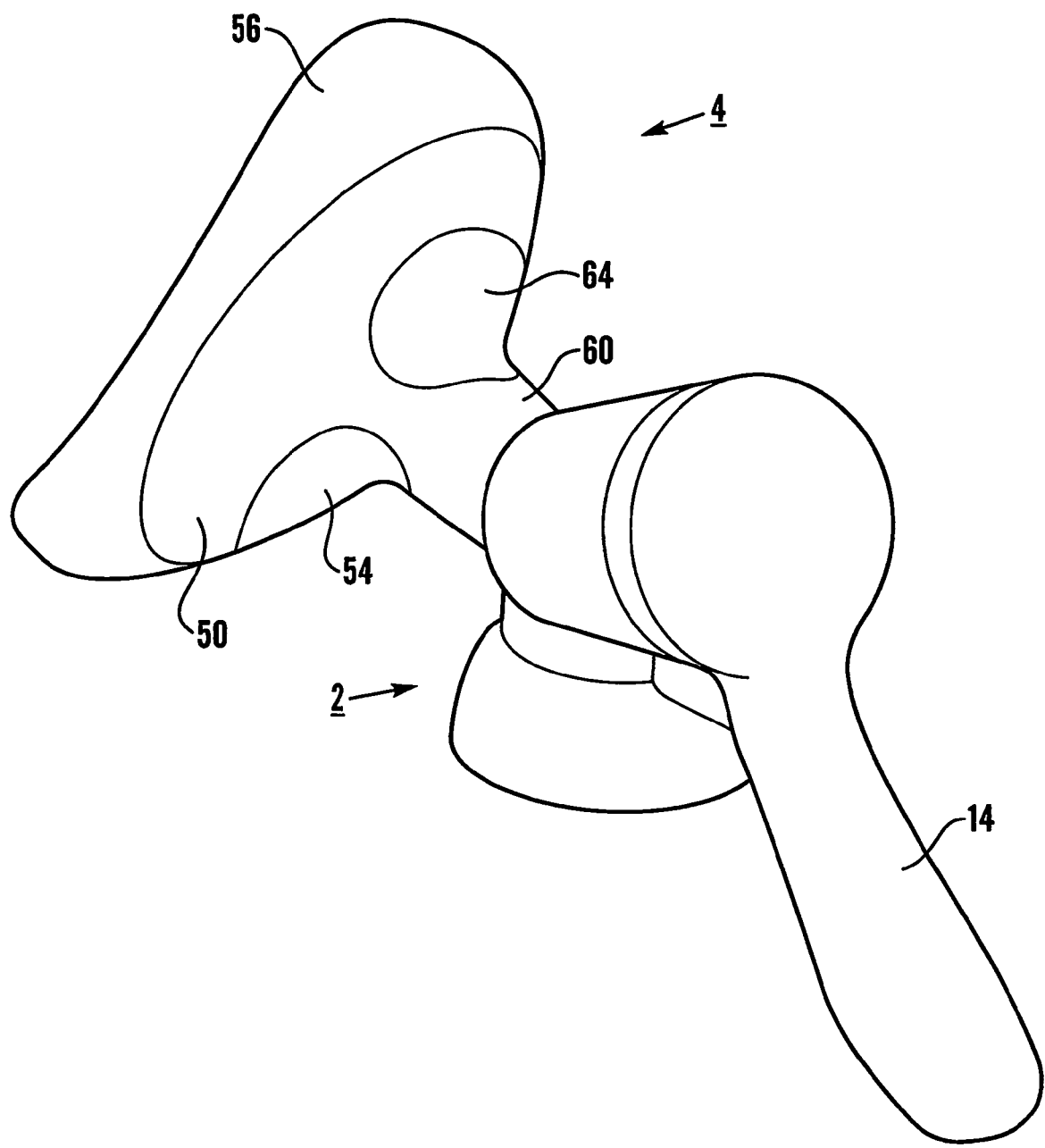
FIG. 9 is an isometric view of part of the pump of FIG. 6.

FIGS. 6 to 8 shows a preferred horn in which there are two opposed apertures in the rigid shell 50, the second aperture being immediately above the first, this second aperture also being infilled at 64 with the soft material to provide opposed regions of soft material which can be manipulated by the user's thumb 60 and finger 62 to stimulate lactation.

It will be appreciated that providing a one-piece horn eliminates the requirement for assembly and disassembly, facilitates cleaning and is safer to use. The presence of the rigid shell 50 supports the breast of the user, while the presence of the infill(s) 54,64 enables manual stimulation of the breast to supplement the effect of the associated pump. The overall lining of the shell 50 with soft material, together with the provision of the lip 56 of said soft material, ensures a comfortable fit of the horn on the user.

Clearly the precise locations and numbers of the infills of soft material can be varied to suit particular requirements, as can the materials of the shell 50 and the layer 52 and the surface configurations thereon.

The invention claimed is:

1. A breast pump comprising a body member including a breast engaging portion shaped to engage a region of a user's breast, a container attached to the body member, and valve means between the body member and the container, characterised by, within the body member, a flexible sleeve sealing the interior of the body member from the atmosphere, the sleeve being selectively movable from a rest condition to a displaced condition by actuating means operatively connected to the sleeve, movement of the sleeve from the rest condition to the displaced condition creating an increasing volume of reduced pressure within the body member whereby firstly the valve means is closed to prevent evacuation of the container, and whereby milk is expressed by the user into the body member, and return movement of the sleeve from the displaced condition to the extended condition releasing the reduced pressure allowing the valve to open the expressed milk flowing through the valve means and into the container, the configuration of the sleeve or the material of the sleeve being such as to substantially prevent stretching of the sleeve on movement between the rest and displaced conditions.

2. A breast pump as claimed in claim 1 in which the sleeve is of generally concertina shape, and is selectively movable between an extended rest condition and a compacted displaced condition.

3. A breast pump as claimed in claim 2 in which the concertina shape has a closed base thereto at least part of which is substantially rigid, movement of the sleeve being by pulling the base from inside the sleeve so as to contract its length.

4. A breast pump as claimed in claim 2 in which the concertina sleeve is of an elastic material the inherent properties of which are such that, on release of the actuating means by the user, the sleeve returns to its extended condition within the body member.

5. A breast pump as claimed in claim 1 in which the sleeve comprises a substantially non-stretch material.

6. A breast pump as claimed in claim 5 in which the sleeve includes a flexible layer to which is bonded or which is inlaid with a substantially non-stretch layer.

7. A breast pump as claimed in claim 1 in which the actuating means comprises a lever arm pivotally mounted at an intermediate region thereof to the body member, one end extent of the lever arm being for engagement by the user, and the other end extent being operatively connected to the sleeve.

8. A breast pump as claimed in claim 1 in which one end of the sleeve is secured between a collar and a defining wall of the body member whereby the interior of the sleeve is sealed from the interior of the body member, the other end of the sleeve being closed.

9. A breast pump as claimed in claim 8 in which the other, closed end of the sleeve carries an end plate, a link pin extending axially within the sleeve and through the collar to interconnect the end plate and the other end extent of the lever arm whereby, on pivoting movement of the lever arm by the user, the link pin is moved substantially axially of the sleeve to compact the sleeve.

10. A breast pump as claimed in claim 9 in which the end plate, link pin, sleeve and lever arm comprise an integral unit.

11. A breast pump as claimed in claim 10 and incorporating flexible joints at one or both ends of the link pin.

12. A breast pump as claimed in claim 1 in which the actuating means comprises an operating member one end of which is secured to a closed end of the sleeve and the other end of which carries a thumb-receiving element for receiving the thumb of a user.

13. A breast pump as claimed in claim 12 in which a handle member is provided as a rest and grip for the fingers of an actuating hand, said handle being rigidly secured to the pump body, the arrangement being such that, on location of the thumb in the thumb-receiving element, and on pulling of the thumb towards the fingers, the base of the sleeve is pulled in the direction generally away from the breast.

14. A breast pump as claimed in claim 1 in which the valve means between the body member and the container comprise a duck bill type one way valve.

15. A breast pump as claimed in claim 1 in which said breast engaging portion comprises a horn made of a rigid material and having bonded thereto at least one region of soft, elastic material, the soft material of the at least one region infilling an associated aperture through the rigid material to comprise the thickness of the horn at said region.

16. A breast pump as claimed in claim 15 in which the rigid material is one of polypropylene and polycarbonate, and the soft elastic material comprises a thermoplastic elastomer.

17. A breast pump as claimed in claim 15 in which there are two opposed regions of soft, elastic material remote from the open end of the horn, one for location above the breast and one for location below the breast adjacent the nipple for manipulation by the thumb and a finger of the user.

18. A breast pump as claimed in claim 15 in which the whole of the internal area of the rigid material is lined with said soft material.

19. A breast pump as claimed in claim 18 in which the outer peripheral edge of the horn comprises a lip of said soft material encasing the periphery of the rigid material.

20. A breast pump as claimed in claim 15 and comprising a two-shot moulding with the soft, elastic material permanently bonded to the rigid material by virtue of the inherent characteristics of the materials.

21. A breast pump comprising a body member including a breast engaging portion shaped to engage a region of a user's breast, a container attached to the body member, and valve means between the body member and the container, characterised by, within the body member, a flexible sleeve sealing the interior of the body member from the atmosphere, the sleeve being selectively movable from a rest condition to a displaced condition by actuating means operatively connected to the sleeve, movement of the sleeve from the rest condition to the displaced condition creating an increasing volume of reduced pressure within the body member whereby firstly the valve means is closed to prevent evacuation of the container, and whereby milk is expressed by the user into the body member, and return movement of the sleeve from the displaced condition to the extended condition releasing the reduced pressure allowing the valve to open the expressed milk flowing through the valve means and into the container, the configuration of the sleeve being such as to substantially prevent stretching of the sleeve on movement between the rest and displaced conditions, wherein the flexible sleeve is of generally concertina shape, and is selectively movable between an extended rest condition and a compacted displaced condition.

22. A breast pump comprising a body member including a breast engaging portion shaped to engage a region of a user's breast, a container attached to the body member, and valve means between the body member and the container, characterised by, within the body member, a flexible sleeve sealing the interior of the body member from the atmosphere, the sleeve being selectively movable from a rest condition to a displaced condition by actuating means operatively connected to the sleeve, movement of the sleeve from the rest condition to the displaced condition creating an increasing volume of reduced pressure within the body member whereby firstly the valve means is closed to prevent evacuation of the container, and whereby milk is expressed by the user into the body member, and return movement of the sleeve from the displaced condition to the extended condition releasing the reduced pressure allowing the valve to open the expressed milk flowing through the valve means and into the container, the material of the sleeve being such as to substantially prevent stretching of the sleeve on movement between the rest and displaced conditions, wherein the flexible sleeve comprises a substantially non-stretch material.

23. A breast pump as claimed in claim 22, wherein said flexible sleeve comprises a layer of elastic material to which is bonded, inlaid or insert molded, a substantially non-stretch layer.

24. A breast pump as claimed in claim 23 wherein said non-stretch layer comprises a fabric mesh.

* * * * *